(12) United States Patent
Copeland et al.

(10) Patent No.: US 6,423,857 B1
(45) Date of Patent: Jul. 23, 2002

(54) METHODS FOR RECOVERING FATTY ACIDS

(75) Inventors: Dick Copeland; W. Maurice Belcher, both of Omaha, NE (US)

(73) Assignee: I.P. Holdings, Omaha, NE (US)

( * ) Notice: Subject to any disclaimer, the term of this patent is extended or adjusted under 35 U.S.C. 154(b) by 0 days.

(21) Appl. No.: 09/808,529

(22) Filed: Mar. 14, 2001

Related U.S. Application Data

(60) Continuation-in-part of application No. 09/550,375, filed on Apr. 14, 2000, now abandoned, which is a division of application No. 09/197,953, filed on Nov. 20, 1998, now Pat. No. 6,172,248.

(51) Int. Cl.$^7$ .................................................. C11B 3/00
(52) U.S. Cl. ...................................... 554/198; 554/212
(58) Field of Search .................................. 554/198, 212

(56) References Cited

U.S. PATENT DOCUMENTS

| | | |
|---|---|---|
| 2,410,926 A | 11/1946 | Bush et al. |
| 4,036,865 A | 7/1977 | Hartmann et al. |
| 4,049,686 A | 9/1977 | Ringers et al. |
| 4,072,482 A | 2/1978 | Aoki et al. |
| 4,240,972 A | 12/1980 | Mag et al. |
| 4,698,185 A | 10/1987 | Dijkstra et al. |
| 4,713,155 A | 12/1987 | Arutjunian et al. |
| 4,996,072 A | 2/1991 | Marschner et al. |
| 5,696,278 A | 12/1997 | Segers |

FOREIGN PATENT DOCUMENTS

| | | |
|---|---|---|
| GB | 701633 | 12/1953 |
| GB | 714160 | 8/1954 |
| LU | 60116 | 12/1969 |
| NL | 18441 | 8/1928 |
| WO | WO 86/04603 | 8/1986 |
| WO | WO 94/12596 | 6/1994 |
| WO | WO 96/41852 | 12/1996 |

OTHER PUBLICATIONS

Patent Abstract of Japan, vol. 1997, No. 10, Oct. 31, 1997, JP 09 154504 (Asahi Denka Kogyo KK), Jun. 17, 1997.
Erickson, David R., Degumming and Lecithin Processing and Utilization, in Practical Handbook of Soybean Processing and Utilization 174, 179–80 (David R. Erickson ed. 1995).
J. C. Schmidt and F.T. Orthoefer, Modified Lecithins, in Lecithins203, 206 (Bernard F. Szuhaj & Gary R. List eds., 1985).
Van Nieuwenhuyzen, W., Lecithin Production and Properties, *J. Amer. Oil Chem. Soc.* 53:425 (1976).

*Primary Examiner*—Deborah D. Carr
(74) *Attorney, Agent, or Firm*—McDonnell Boehnen Hulbert & Berghoff

(57) ABSTRACT

This invention relates to improved methods for recovering fatty acids during purification of vegetable oil. More particularly, this invention relates to improved methods for recovering fatty acids from a phosphatide-containing material obtained from organic acid refining of vegetable oil.

8 Claims, 1 Drawing Sheet

METHODS FOR RECOVERING FATTY ACIDS

CROSS-REFERENCE

This application is a continuation-in-part of U.S. patent application Ser. No. 09/550,375, filed Apr. 14, 2000, which is a divisional of U.S. patent application Ser. No. 09/197,953, filed Nov. 20, 1998, now U.S. Pat. No. 6,172,248.

FIELD OF THE INVENTION

This invention relates to improved methods for recovering free fatty acids during purification of vegetable oil. More particularly, this invention relates to improved methods for recovering free fatty acids from a phosphatide-containing material obtained from organic acid refining of vegetable oil.

BACKGROUND OF THE INVENTION

Free fatty acids and phosphatides are two of several byproducts recoverable during the purification of vegetable oil. Vegetable oils are typically obtained by pressing or extracting the oil seeds of plants such as corn or soybeans. Vegetable oils primarily consist of triglycerides, also termed triacylglycerols. In addition to triglycerides, however, vegetable oils also contain several other compounds. Some of these additional compounds, such as mono- and di-glycerides, tocopherols, sterols, and sterol esters, need not necessarily be removed during processing. Other compounds and impurities such as phosphatides, free fatty acids, odiferous volatiles, colorants, waxes, and metal compounds negatively affect taste, smell, appearance and storage stability of the refined oil, and hence must be removed. Carefully separated, however, some of these additional compounds, particularly the phosphatides, are valuable raw materials.

Vegetable oil triglycerides are esters of 1,2,3-propane triol, also termed glycerol, and can be represented by the generic formula

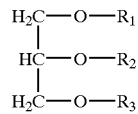

where $R_1$, $R_2$, and $R_3$ are the same or different, and are selected from the group consisting of $C_{10}$-$C_{22}$ saturated and unsaturated fatty acids. In soybean oil in particular, the saturated fatty acids that can occur include but are not limited to lauric (C12:0), myristic (C14:0), palmitic (C16:0), stearic (C18:0), arachidic (C20:0), and behenic (C22:0) acids. Generally, however, the fatty acids of soybean oil are predominantly unsaturated, and include but are not limited to oleic (C18:1), linoleic (C18:2), and linolenic (C18:3) acids. Unsaturated fatty acids can exist as geometric and/or positional isomers, each such isomer having different properties such as melting point. Naturally occurring fatty acids generally exist in the cis form, but they can be converted into the trans form during the course of purification steps used to produce a vegetable oil from an oilseed. Crude soybean oil in particular typically contains from about 95 to about 97 percent by weight triglycerides, composed primarily of unsaturated fatty acids, together with usually not more than about 1.5 percent by weight free fatty acids and from about 1.5 to about 3 percent by weight of phosphatides, depending on the kind and quality of soybean and oilseed processing procedures.

Free Fatty Acids

The free fatty acid content of a vegetable oil comprises the amount of fatty acid present in an uncombined state as a chemical unit, i.e., not esterified on the glycerol backbone of triglycerides or phosphatides. Free fatty acids originate from the breakdown of triglycerides into its component fatty acid and glycerol units, and result from exposure of triglycerides to moisture and/or from enzymatic processes triggered by damage to the oilseed, such damage caused for example by splitting, breaking, or by heating or other damage induced during storage.

The free fatty acid content of vegetable oil will vary based on a number of factors, including but not limited to oilseed type, seed quality, and the process by which oil is extracted therefrom. Crude vegetable oil typically contains from about 0.2 and to about 5 percent by weight free fatty acids. With soybean oil in particular, a normal-quality crude oil generally contains between about 0.2 and 0.5 percent by weight free fatty acids; however, poorer-quality crude soybean oil may contain free fatty acids in excess of 1 percent by weight. Free fatty acids present in vegetable oils generally comprise the same $C_{10}$ to $C_{22}$ saturated and unsaturated fatty acids that are present in the triglycerides, as described in detail above.

A high free fatty acid content in a refined vegetable oil generally indicates that the oil was poorly processed or that there has been some triglyceride breakdown after manufacture. Free fatty acids can be valuable materials, however, when properly removed from crude vegetable oil.

Phosphatides

The terms phosphatides or phosphatide concentrates are commonly used to refer to a mixture of phospholipids comprising phosphatidyl derivatives which are present in crude vegetable oil. Such phosphatides also are referred to as gums. After being removed from vegetable oil by treatment with water, phosphatides are often called wet gums or wet lecithin. Upon being dried, phosphatides generally are termed lecithin or commercial lecithin. Crude soybean oil in particular provides the chief source for commercial lecithin.

The term lecithin, from a true chemical sense, refers to phosphatidyl choline. However, as used by commercial suppliers, the term lecithin refers to a product derived from vegetable oils, especially soybean oil. Specific chemical components of phosphatides present in vegetable oil include phosphatidyl choline, 1; phosphatidylethanolamine, 2; phosphatidylinositol, 3; phosphatidyl serine, 4; phosphatidic acid, 5; cyclolipids, and other components such as free sugars, metals and free fatty acids.

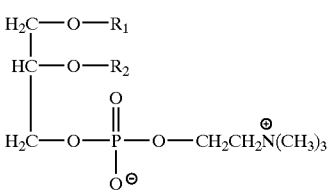

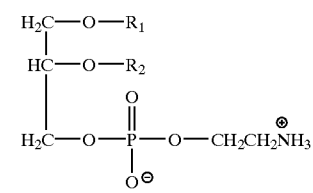

-continued

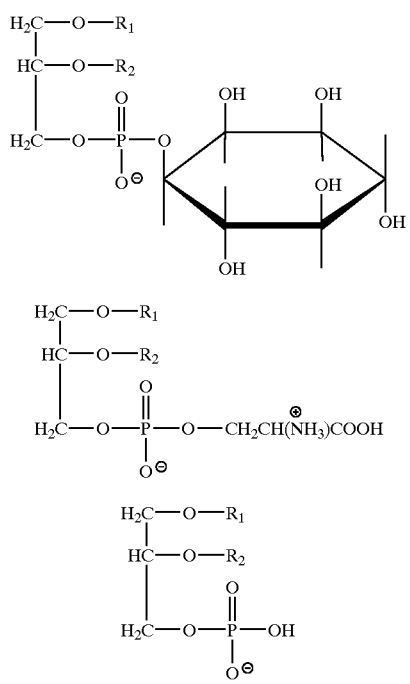

Such phosphatides are amphipathic, i.e. one end of the molecule is hydrophilic (lipophobic) and the other end is hydrophobic (lipophilic). As a result, they possess useful surface-active properties, and can orient in aqueous environments to create membranes and bilayers.

The fatty acid content of the phosphatides 1 through 5 is represented by $R_1$ and $R_2$, as defined above, and previously has been thought to match that of the vegetable oil from which the phosphatides are derived. The phosphatide content of vegetable oil will vary based on a number of factors, including but not limited to oilseed type, seed quality, and the process by which oil is extracted therefrom. Crude soybean oil in particular typically contains from about 1.5 to about 3 percent by weight phosphatides. Phosphatides comprise both hydratable phosphatides (HPs) and non-hydratable phosphatides (NHPs). Although non-hydratable phosphatides tend to remain oil-soluble and are largely unaffected by water, hydratable phosphatides when hydrated become greater in density than the triglycerides and precipitate, or settle out. This phenomenon forms the basis for the process of conventional water degumming, discussed more fully below.

Recovery of Phosphatides From Vegetable Oils

Vegetable oil impurities are typically removed in four distinct steps of degumming, refining, bleaching, and deodorizing. Of these four steps, degumming removes the largest amount of impurities, the bulk of which are hydratable phosphatides. Refining primarily removes non-hydratable phosphatides, soaps created from the neutralization of free fatty acids, and other impurities such as metals. Bleaching then improves the color and flavor of refined oil by decomposing peroxides and removing oxidation products, trace phosphatides, and trace soaps. Soybean oil bleaching materials include neutral earth (commonly termed natural clay or fuller's earth), acid-activated earth, activated carbon, and silicates. Deodorizing is the final processing step and prepares the oil for use as an ingredient in many edible products including salad oils, cooking oils, frying fats, baking shortenings, and margerines. The deodorizing process generally comprises passing steam through refined oil at high temperature and under near vacuum conditions to vaporize and carry away objectionable volatile components.

Vegetable oil refining, also known as neutralization or deacidification, essentially involves removing free fatty acids (FFA) and phosphatides from the vegetable oil. Most refining operations employ either alkali refining (also termed caustic refining) or physical refining (also termed steam refining). Of these two refining methods, alkali refining predominates.

For either refining method, an optional but preferred first step is a conventional water degumming process. Degumming refers to the process of removing hydratable phosphatides and other impurities such as metals from vegetable oils. A simple degumming process comprises admixing demineralized water with the vegetable oil and separating the resulting mixture into an oil component and an oil-insoluble hydrated phosphatides component (frequently referred to as a "wet gum" or "wet lecithin"). The NHPs, generally considered to be calcium and magnesium salts of phosphatidic acids, are largely unaffected by water and remain soluble in the oil component. Phosphatidic acids are typically produced via the action of phospholipidases, which are released from the oil seed upon damage to the cellular structure.

Normally, refiners also must introduce chelating agents following degumming processes to remove metal compounds from crude vegetable oil, which typically contains calcium, potassium, magnesium, aluminum, iron and copper. Left in place, these metal impurities form salts of phosphatidic acid, thereby contributing to the NHP content. Moreover, metal contaminants, especially iron, can darken oil during deodorization, and even small amounts of iron that do not affect the oil's color can nevertheless dramatically reduce stability of refined oil.

Treating crude vegetable oil with demineralized water produces a degummed oil and a phosphatide concentrate containing the hydratable phosphatide fraction. This phosphatide concentrate subsequently can be removed from the degummed oil by a convenient method such as by gravitational force or by centrifugal separation. Phosphatide concentrates coming from centrifugal separation will generally contain up to about fifty percent by weight water, and typically will contain from about twenty-five to about thirty percent by weight water. In order to minimize chances of microbial contamination, phosphatide concentrates must be dried or otherwise treated immediately. Dried phosphatide concentrates can be profitably sold as commercial lecithin. Degummed oil is further refined to remove NHPs and other unwanted compounds.

Mineral acid also is sometimes added during the water degumming process to help minimize the NHP content of degummed oil. The acid combines with calcium and magnesium salts, enabling phosphatidic acids to migrate from the oil to the water phase, thus eliminating them from the crude oil. However, using mineral acid during degumming is inappropriate when seeking to recover gums intended for use as lecithin because the presence of mineral acid will cause darkening of the lecithin.

In alkali refining, free fatty acids and gums are removed from crude or degummed oil by mixing the oil with a hot, aqueous alkali solution, producing a mixture of so-called neutral oil and soapstock (also termed refining byproduct lipid), which is an alkaline mixture of saponified free fatty acids and gums. The neutral oil is then separated from the soapstock, typically by centrifugation. The soapstock has commerical value due to its fatty acid content but must be processed further in order to render it salable. The neutral oil is further processed to remove residual soap.

The alkali refining process has several drawbacks, however. One drawback is that alkali refining allows recovering only the hydratable phosphatide fraction, because the non-hydratable phosphatide fraction is destroyed and converted into materials that wind up in the soapstock. And although employing mineral acids during water degumming can reduce the overall NHP content prior to alkali treatment by converting the NHPs into water-soluble forms, thus potentially increasing the percentage recovery of the overall phosphatide fraction, using mineral acids during degumming causes undesirable darkening of lecithin.

An alternative to alkali refining is physical refining. Physical refining is a steam distillation process essentially the same as that used in conventional vegetable oil deodorization processes, in which steam passing through vegetable oil vaporizes and carries away free fatty acids. The main advantage of physical refining over alkali refining is that no soapstock is generated. A second advantage is lower refining losses because there is no saponification of oil and no oil emulsifaction by soapstock.

Accordingly, there is significant interest in physical refining due to its economic advantages and friendliness compared to alkali refining. But because physical refining does not remove NHPs, any oils to be physically refined must be free of NHPs in order to ensure stable refined oils. Oils such as palm oil and tallow, which have low NHP content, can be successfully physically refined. But oils such as soybean oil and sunflower seed oil, which are relatively high in NHPs, are not commonly physically refined because the pre-refining step of water degumming does not remove NHPs. Moreover, physically refined soybean oils have only limited acceptance in the U.S. market due to their lack of flavor stability.

One recent and attractive alternative route to obtaining phosphatide-containing mixtures is organic acid refining of vegetable oil, as disclosed in pending U.S. patent application Ser. No. 09/197,953. In an organic acid refining process, a dilute aqueous organic acid solution is admixed with a heated stream of crude vegetable oil to give an acid-oil blend. The acid-oil blend is thereafter subjected to high shear for a time sufficient to finely disperse the dilute aqueous organic acid solution in the crude vegetable oil and give an acid-and-oil mixture, which is also termed a phosphatide-containing mixture, and/or is subjected to low shear for a time sufficient to produce a phosphatide-enriched aqueous phase (also termed a hydrated impurities phase) into which oil contaminants are sequestered and also produce a purified vegetable oil phase.

Vegetable oils suitable for organic acid refining include but are not limited to those derived from soybean oil, corn oil, cottonseed oil, palm oil, peanut oil, rapeseed oil, safflower oil, sunflower seed oil, sesame seed oil, rice bran oil, coconut oil, canola oil, and mixtures thereof. A particularly preferred vegetable oil is soybean oil.

The dilute aqueous organic acid solution may be prepared from any food grade organic acid, including but not limited to phosphoric acid, acetic acid, citric acid, tartaric acid, succinic acid, or combinations thereof. A particularly preferred organic acid is citric acid. Using a food grade organic acid, as opposed to a mineral acid, ensures that phosphatides removed during the purifying process can be purified and sold as commercial lecithin to the food industry. Using an organic acid also enables sequestering metal contaminants without the need to add other chelating agents. In preparing the dilute aqueous organic acid solution, demineralized water is preferably used. Using demineralized water avoids the possibility of converting hydratable phosphatides to non-hydratable phosphatides. As used herein, the term demineralized water means water substantially devoid of calcium and magnesium ions.

The dilute aqueous organic acid solution has a concentration based on the combined weight of organic acid and water of from about 1 to about 5 percent by weight. The dilute aqueous organic solution is combined with the heated vegetable oil in a ratio of from about 3:97 to about 20:80, depending on the source from which the vegetable oil is derived and on whether the vegetable oil has been degummed.

The phosphatide-containing mixture generally comprises hydratable phosphatides, nonhydratable phosphatides that have been converted into water-soluble form, water, organic acid, and vegetable oil, as well as other contaminants including but not limited to metals. The phosphatide-containing mixture may be mixed at low shear for a time of less than about 16 minutes to allow sequestering of contaminants, especially metals, into the phosphatide-enriched aqueous phase. The term sequestering as used herein refers to the process wherein contaminants are either directly or indirectly (through chemical conversion into water-soluble forms) taken up into the phosphatide-enriched aqueous phase.

In one mode of organic acid refining, the phosphatide-containing mixture is separated into its component parts in a stepwise fashion, the first step of which is separation into two streams comprising a purified vegetable oil phase and a phosphatide-enriched aqueous phase. Separation can occur by any convenient method, including by centrifugation or by permitting the phosphatide-containing mixture to settle for a time sufficient to develop a purified vegetable oil phase and a phosphatide-enriched aqueous phase. This route can be employed because the purified vegetable oil typically separates fairly quickly from the phosphatide-enriched aqueous phase. The purified vegetable oil phase can be further processed, as for example by bleaching and deodorizing, and subsequently used or sold. The phosphatide-enriched aqueous phase can be dried or it can undergo further processing.

The phosphatide-enriched aqueous phase itself comprises an aqueous organic acid phase and an organic acid-treated phosphatide phase. Accordingly, a second separation step can be used to isolate one of these two remaining phases from the other. Once isolated, the aqueous organic acid phase can be recycled without further treatment into the organic acid refining process. The organic acid-treated phosphatide phase can be further processed.

In another mode of organic acid refining, the phosphatide-containing mixture is separated directly into three component parts comprising a purified vegetable oil phase, an organic acid-treated phosphatide phase, and an aqueous organic acid phase. Separation advantageously occurs by permitting the phosphatide-containing mixture to remain unagitated for a time sufficient to develop discrete phases. Typically, the purified vegetable oil phase migrates to the top, the organic acid-treated phosphatide phase migrates to the middle, and the aqueous organic acid phase migrates to the bottom. Once discrete phases exist, they can be separated from each other in any order. Typically, however, the purified vegetable oil phase is separated first, and then one of the two remaining phases is separated from the other. As above, the purified vegetable oil phase can be further processed, as for example by bleaching and deodorizing, and subsequently used or sold. The aqueous organic acid phase can be recycled without further treatment into the organic acid refining process. The organic acid-treated phosphatide phase can be further processed. Thus, alternate modes of organic acid refining produce either a phosphatide-enriched aqueous phase or a more concentrated organic acid-treated phosphatide phase, which, alone or in combination, can be further processed.

Once isolated from vegetable oils, phosphatides are usually subjected to further processing to produce lecithins. Lecithins are utilized in a broad variety of applications and perform an array of valuable functions. In edible compositions, lecithin contributes nutritional value and also can act as an emulsifying agent, surface-active agent, antispattering-agent, or stabilizing agent. Lecithin can be used in technical applications as an anti-foam agent, dispersing agent, wetting agent, stabilizing agent, and as an anti-knock compound for gasoline formulations. In particular, in foods such as baked goods or margarine, lecithin is used as a dispersing agent, emulsifier, viscosity reducer and antioxidant. In cosmetics such as shampoos or skin lotions, lecithin is employed as a foam stabilizer, emollient, emulsifier, and wetting agent. In pharmaceuticals targeted for either topical or parenteral administration, lecithin functions as softening agent, carrier, emulsifier, and penetration enhancer. Lecithin also possesses unique release properties, and is useful in pan-frying and pan grease formulations for baking, as well as in mold release formulations which enable casting forms to be easily removed.

Changes in lecithin functionality and physicochemical properties can be made using various modification techniques. For example, fractionating lecithin in ethanol changes the ratio of phosphatidylcholine to phosphatidylethanolamine to produce a material having improved oil-in-water emulsifying ability. Acetylation using acetic anhydride also improves oil-in-water emulsifying ability. Hydroxylation using hydrogen peroxide and lactic acid or a peracid improves oil-in-water emulsifying ability and water dispersibility. Hydrolysis of lecithin, normally achieved either via action of strong base or acid or via enzymatic action, provides a material having improved hydrophilic and emulsifying properties. Enzymatically modified lecithins incorporated into animal feed formulations can improve emulsification and digestibility of fats. In some animal studies, such hydrolyzed lecithins, also termed lysolecithins, were shown to be more rapidly absorbed following oral administration.

Lecithin varies in appearance from highly viscous to semiliquid to powder, and generally is brown in color. Hydrolyzed lecithin, also termed lysolecithin and lysophosphatidylcholine (LPC), is a desirable modified form of lecithin and generally comprises a highly viscous or pasty fluid ranging in color from light brown to brown. The composition of several lecithins derived from vegetable oil is shown in Table 1. The fatty acid composition of lecithin derived from soybean oil in particular is shown in Table 2.

TABLE 1

Composition of Various Oil-Free Lecithins (%) Derived From Vegetable Oils

| Phosphatide Component | Soybean | Corn | Sunflower | Rapeseed |
|---|---|---|---|---|
| Phosphatidyl Choline | 12–46 | 31 | 14 | 37 |
| Phosphatidyl Ethanolamine | 8–34 | 3 | 24 | 29 |

TABLE 1-continued

Composition of Various Oil-Free Lecithins (%) Derived From Vegetable Oils

| Phosphatide Component | Soybean | Corn | Sunflower | Rapeseed |
|---|---|---|---|---|
| Phosphatidyl Inositol | 1.7–21 | 16 | 13 | 14 |
| Phosphatidyl Serine | 0.2–6.3 | 1 | — | — |
| Phosphatidic Acid | 0.2–14 | 9 | 7 | — |
| Glycolipids | 14.3–29.6 | 30 | — | 20 |

TABLE 2

Fatty Acid Composition (% Range) of Lecithin Derived From Soybean Oil

| Fatty Acid | Percent by Weight |
|---|---|
| Palmitic | 11.7–42.7 |
| Stearic | 3.7–11.7 |
| Oleic | 6.8–39.4 |
| Linoleic | 17.1–60.8 |
| Linolenic | 1.6–9.2 |

Commercial lecithin is typically produced in a continuous process by drying phosphatide concentrates, which are obtained as byproducts of vegetable oil purification processes, at a temperature of from 176° F. to 203° F. and at an absolute pressure of from about 50 mm Hg to about 300 mm Hg. Erickson, David R., *Degumming and Lecithin Processing and Utilization*, in Practical Handbook of Soybean Processing and Utilization 174, 179–80 (David R. Erickson ed. 1995); Van Nieuwenhuyzen, W., *J Amer. Oil Chem. Soc.* 53:425 (1976). If mistreated during drying, however, lecithin can have an objectionable odor and flavor that is difficult to remove. Phosphatides easily oxidize when subjected to heating, and such oxidative products can contribute a bitter or rancid taste to lecithin. Heating of phosphatides can also induce formation of volatile decomposition products such as 4,5-dimethylisoxazole, which contributes an objectionable flavor to lecithin. Other volatile compounds such as isophorone, a contributor of objectionable odor, can form by an aldol condensation reaction involving solvent remaining from crude vegetable oil refining processes. Thus, care must be exercised in the method used to remove objectionable volatile components from lecithin.

Recovery of Free Fatty Acids From Vegetable Oil

Different methods are employed to recover free fatty acids from crude vegetable oils, depending on the refining method selected. Historically, however, all such methods have focused on recovering fatty acids in various ways from the oil portion. Accordingly, free fatty acids isolated via these methods can be termed oil-derived free fatty acids.

When alkali refining is selected, the free fatty acids initially present in the crude vegetable oil end up in the soapstock. The bulk of the free fatty acids are recovered by acidulation of soapstock. Soapstock produced during alkali refining generally contains from about 30 to about 50 percent by weight fatty acids, as well as from about 25 to about 60 percent by weight water and from about 3 to about 12 percent by weight non-fatty components, including non-hydratable phosphatides. Deodorizer distillate produced from alkali-refined oil generally contains from about 40 to about 60 percent by weight fatty acids.

Soapstock contains fatty acids present in the form of fatty acid soaps, triglycerides, and phosphatides. Soapstock acidulation typically involves partitioning the soapstock into separate oil and aqueous phases by adding a mineral acid, usually aqueous sulfuric acid, and then boiling the mixture, usually with sparge steam, for 2 to 4 hours. Adding mineral acid reduces the pH to below 2 and liberates free fatty acids from their alkali metal soaps. Because the aqueous phase is heavier than the oil phase, the oil phase (termed acid oil) rises to the top and the aqueous phase (termed acid water) settles to the bottom, the phases can be separated by centrifugation or gravity. Generally, the mixture is allowed to settle and the acid oil layer is decanted off. The acid oil is then washed with about 25 to 50 percent by weight water, boiled for a short period, and the mixture is allowed to settle. Thereafter, the water layer is drawn off and the remaining product, termed acidulated soapstock, is sold as an animal feed ingredient or can be further processed to recover fatty acids.

Acidulated soapstock contains about 20 to 30 percent by weight triglycerides, 65 to 70 percent by weight fatty acids, and about 5 percent by weight tocopherols, sterols, and other impurities. When free fatty acid recovery is desired, acidulated soapstock is generally subjected to vacuum distillation, producing a free fatty acid vapor stream that is condensed to produce a free fatty acid distillate. In certain cases where the still residue contains a significant free fatty acid content, such residue can be subjected to re-saponification, re-acidulation, re-separation of the aqueous and fatty acid-containing oil phases, and re-distillation of the fatty acid-containing acidulated soapstock phase to recover additional free fatty acid distillate.

Some refiners seek to avoid the step of vacuum distilling the acidulated soapstock by preboiling soapstocks with excess alkali to saponify neutral oil components before acidulation and thereby maximize formation of fatty acid soaps. Acidulated preboiled soapstocks generally contain greater than about 90 percent by weight free fatty acids, and only minor amounts of triglycerides and other non-free fatty acid impurities.

In alkali refining, a small amount of free fatty acids remain in the degummed oil and are carried forward to the deodorization step. These additional free fatty acids can be recovered by treatment of the distillate produced during deodorization. In a typical deodorization process, free fatty acids and other volatiles such as tocopherols and sterols are vaporized away from the feedstock. The vapor stream is then condensed to form a deodorizer distillate, which can be further processed. However, separating the free fatty acids from the tocopherols and sterols in the deodorizer distillate is complicated and expensive. Moreover, because alkali treatment itself has reduced the free fatty acid content of the pre-deodorizer oil to a level below about 0.05 percent by weight, the investment in time and equipment required to effect recovery of fatty acids often outweighs the value to be gained by producing such fatty acids.

When physical refining is selected, free fatty acids are recovered during a steam distillation process that is essentially the same as that used in conventional vegetable oil deodorization processes, wherein steam passing through vegetable oil vaporizes and carries away free fatty acids. However, because physical refining of an oil does not entail reducing its free fatty acid content prior to sending it to the deodorizer, the pre-deodorizer oil in a physical refining process contains much more free fatty acid compared to the pre-deodorizer oil in alkali refining. Typically, the free fatty acid level of pre-deodorizer oil in a physical refining process ranges from about 0.2 to about 1 percent by weight. Thus, the distillate treatment steps leading to free fatty acid recovery that can prove unprofitable when treating deodorizer distillate resulting from deodorizing alkali-refined oil, generally can be profitable when treating deodorizer distillate resulting from physically-refined oil.

Oil-derived fatty acids recovered via the methods described above generally have the same chain length distribution as that of the triglycerides from which they were produced. Such fatty acids typically range in color from about a Gardner 6 to about a Gardner 10. Free fatty acids produced from the various processes described above can be used as is or can be purified into fractions of individual free fatty acids by further distillation or fractionation. Such free fatty acids and fractions thereof can be advantageously converted into a wide variety of oleochemicals, such as dimer and trimer acids, diacids, alcohols, amines, amides, and esters.

As discussed above, however, previously known methods for obtaining free fatty acids generally have required lengthy and costly processing steps. Consequently, further improvements in obtaining free fatty acids have been sought. The present invention relates to improved processes having advantages over those previously disclosed. The processes of the invention produce free fatty acids directly and simply from either a phosphatide-enriched aqueous phase or an organic acid-treated phosphatide phase, both of which are obtained from an organic acid refining process.

SUMMARY OF THE INVENTION

One aspect of the present invention relates to a process that produces free fatty acids from a phosphatide-containing material selected from the group consisting of a phosphatide-enriched aqueous phase obtained from an organic acid refining process, an organic acid-treated phosphatide phase obtained from an organic acid refining process, or a mixture thereof.

Another aspect of the invention relates to a process that produces a free fatty acid-containing distillate that is white.

Another aspect of the invention relates to a process that produces a distillate containing palmitic and oleic acids in a ratio of at least about 1.5:1.

One embodiment of the invention is a process for recovering free fatty acids from an organic acid-treated phosphatide that comprises the steps of providing a phosphatide-containing material selected from the group consisting of a phosphatide-enriched aqueous phase obtained from an organic acid refining process, an organic acid-treated phosphatide phase obtained from an organic acid refining process, or a mixture thereof; maintaining the phosphatide-containing material at acidic pH for a time sufficient to produce a reaction mixture containing free fatty acids; distilling the reaction mixture for a time sufficient to convert the reaction mixture into a vapor phase and a liquid residue; and condensing the vapor phase to form a distillate containing at least about 97 percent by weight free fatty acids.

Another embodiment of the invention is a process for recovering free fatty acids from an organic acid-treated phosphatide that comprises the steps of providing a phosphatide-containing material selected from the group consisting of a phosphatide-enriched aqueous phase obtained from an organic acid refining process, an organic acid-treated phosphatide phase obtained from an organic acid refining process, or a mixture thereof; maintaining the phosphatide-containing material at acidic pH for a time sufficient to produce a reaction mixture containing free fatty acids; distilling the reaction mixture in a dryer utilizing an operating pressure of less than about 4 mm Hg and a temperature of less than about 440° F. for a time sufficient to convert the reaction mixture into a vapor phase and a liquid residue; and condensing the vapor phase to form a distillate containing at least about 97 percent by weight free fatty acids.

Yet another embodiment of the invention is a process for recovering free fatty acids from an organic acid-treated phosphatide that comprises the steps of providing a phosphatide-containing material selected from the group consisting of a phosphatide-enriched aqueous phase obtained from an organic acid refining process, an organic acid-treated phosphatide phase obtained from an organic acid refining process, or a mixture thereof; maintaining the phosphatide-containing material at acidic pH for a time sufficient to produce a reaction mixture containing free fatty acids; distilling the reaction mixture in a deodorizer utilizing an operating pressure of less than about 4 mm Hg and a temperature of less than about 440° F. for a time sufficient to convert the reaction mixture into a vapor phase and a liquid residue; and condensing the vapor phase to form a distillate containing at least about 97 percent by weight free fatty acids.

These and other aspects of the invention will become apparent in light of the detailed description below.

DESCRIPTION OF A PREFERRED EMBODIMENT

Figure 1:
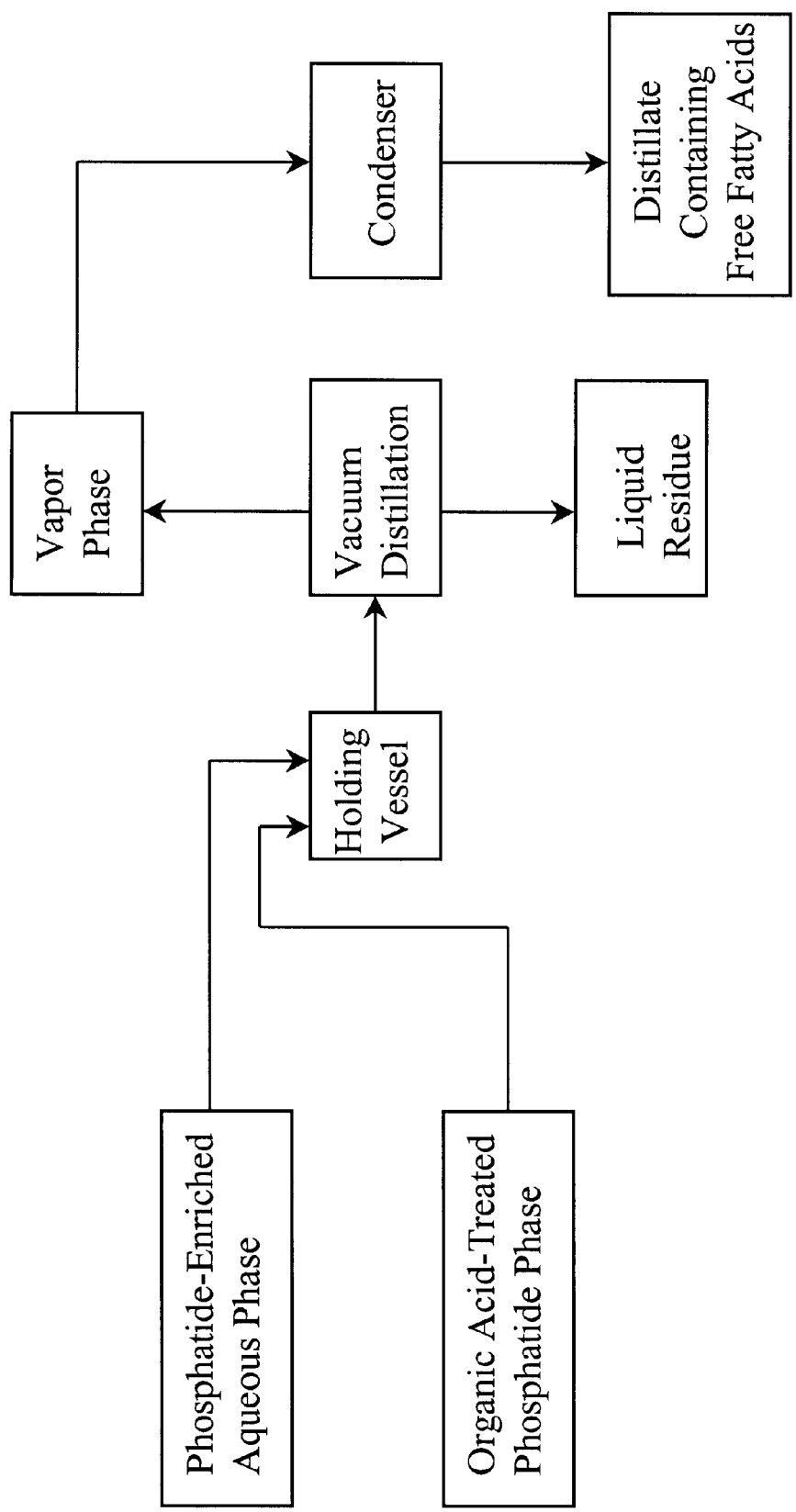
FIG. 1 is a block diagram depicting a process of the invention.

Phosphatide-containing materials suitable for use in processes of the invention can be obtained from organic acid refining of vegetable oil, as disclosed in pending U.S. patent application Ser. No. 09/550,375, U.S. patent application Ser. No. 09/514,838, and U.S. patent application Ser. No. 09/197,953, herein incorporated by reference in their entirety.

As illustrated in the block diagram of FIG. 1, the invention generally entails providing a phosphatide-containing material; optionally but preferably maintaining the phosphatide-containing material in a holding vessel for a certain time; maintaining the phosphatide-containing material at acidic pH for a time sufficient to produce a reaction mixture containing free fatty acids; distilling the reaction mixture for a time sufficient to convert the reaction mixture into a vapor phase and a liquid residue; and condensing the vapor phase to form a distillate containing free fatty acids. The improved processes of the invention for recovering fatty acids can be conducted as batch or continuous processes.

The improved processes disclosed herein begin by providing a phosphatide-containing material selected from the group consisting of a phosphatide-enriched aqueous phase obtained from an organic acid refining process, an organic acid-treated phosphatide phase obtained from an organic acid refining process, or a mixture thereof. Preferred phosphatide-containing materials are those resulting from citric acid refining of soybean oil.

A phosphatide-enriched aqueous phase generally comprises water, organic acid, and an organic acid-treated phosphatide which itself comprises hydratable phosphatides and nonhydratable phosphatides that have been converted into water-soluble form. A phosphatide-enriched aqueous phase typically comprises from about 30 to about 70 percent by weight water and has a pH of from about 2 to about 4.

An organic acid-treated phosphatide phase generally comprises water, hydratable phosphatides, and nonhydratable phosphatides that have been converted into water-soluble form. An organic acid-treated phosphatide phase typically comprises from about 20 to about 50 percent by weight water and has a pH of from about 2.5 to about 3. Thus, an organic acid-treated phosphatide is more concentrated than a phosphatide-enriched aqueous phase, and accordingly has a more acidic pH. When the phosphatide-containing material comprises a mixture of a phosphatide-enriched aqueous phase and an organic acid-treated phosphatide phase, the two phases can be combined in any ratio. Generally, however, in such mixtures the organic acid-treated phosphatide phase predominates. Either or both of the phases can be supplied from storage or can be supplied as a continuous output stream of an organic acid refining process.

Once provided, the phosphatide-containing material is maintained at acidic pH for a time sufficient to produce a reaction mixture containing free fatty acids. The term acidic pH as used herein means a pH of less than about 7. The phosphatide-containing material can be maintained at acidic pH for the desired time either by circulating it in a continuous loop or by simply maintaining it in a holding vessel.

Maintaining the phosphatide-containing material at acidic pH produces free fatty acids via acid hydrolysis that causes fatty acid moieties to be cleaved from the glycerol backbone of the phosphatides. The phosphatide-containing material is maintained at acidic pH until acid hydrolysis causes greater than about 75 percent of the fatty acid moieties to be cleaved from the phosphatides. Because free fatty acids of the invention are produced from the phosphatides, they are termed phosphatide-derived fatty acids, to distinguish them from the oil-derived fatty acids that previously have been the only fatty acids available as byproducts of vegetable oil refining.

Because the phosphatide-containing material itself already has a fairly acidic pH, further pH adjustment is not necessary to promote acid hydrolysis. Acid hydrolysis will occur more rapidly, however, as the fraction of organic acid-treated phosphatide phase in the phosphatide-containing material increases, because the pH of the organic acid-treated phosphatide phase is more acidic than that of the phosphatide-enriched aqueous phase. Generally, when the phosphatide-containing material is an organic acid-treated phosphatide phase and no further pH adjustment is made, the phosphatide-containing material maintains a pH of about 3.5, and about 6 hours is required to produce a reaction mixture containing free fatty acids. Optionally, however, in order to hasten acid hydrolysis and thereby reduce the amount of time required to cleave fatty acid moieties from the phosphatides, the pH of the phosphatide-containing material can be made even more acidic by adding any pH-lowering (i.e. acid) ingredient. If this route is selected, the pH-lowering (acid) ingredient added is preferably an aqueous organic acid or a mineral acid, and most preferably is sulfuric acid. When a pH-lowering (acid) ingredient is added, it is generally employed in an amount sufficient to lower the pH to a value of about 3. Generally, when the phosphatide-containing material is adjusted to and maintained at a pH of about 3, about 6 hours is required to produce a reaction mixture containing free fatty acids.

Once the reaction mixture containing free fatty acids is formed, it is then distilled for a time sufficient to convert the reaction mixture into a vapor phase and a liquid residue. Such distillation generally produces vapor phase in an amount of greater than about 10 percent by weight of the reaction mixture. The vapor phase contains at least about 97 percent by weight free fatty acids. The liquid residue is produced in an amount of greater than about 40 percent by weight of the reaction mixture and contains at least about 90 percent by weight total fatty acids. Because the total fatty acid content of the liquid residue is at least about 90 percent by weight, it is a food grade material that can be profitably sold as an animal feed. The vapor phase can be condensed into a distillate, as discussed more fully below.

The reaction mixture can be distilled in any convenient apparatus capable of operating at a pressure below about 6 mm Hg and a temperature of less than about 460° F. Devices commonly available in a vegetable oil refinery and which are suitable for distilling the reaction mixture include but are not limited to dryers and deodorizers. In either device, the reaction mixture is subjected to elevated temperature and reduced pressure conditions at which free fatty acids vaporize and are carried away from the still residue.

Two types of dryers are widely utilized in vegetable oil refineries. One type, vacuum batch dryers, operate at a vacuum of from about 27 to about 29 inches of water and are equipped with rotating ball-shaped coils through which water circulates to maintain an interior temperature of 140–160° F. The other type of dryer, an agitated-film or thin-film evaporator, is much more prevalent, particularly in the United States. Thin film evaporators operate at a vacuum of from about 29 inches of water to about 2 mm Hg and a temperature of 175–225° F.

Either a batch-type or a continuous drying process will suffice, but continuous drying is preferred. More preferred is a continuous agitated-film dryer. Most preferably, drying occurs on a thin-film dryer such as a Votator Turba Film available from L.C.I. Corp. Advantageously, the reaction mixture is heated to a temperature of from about 120° F. to about 140° F. prior to being introduced into the dryer.

Drying under reduced pressure is preferred. Reduced pressure can be generated by any convenient source. Steam jet ejector systems are commonly employed. Most preferred is to use a Nash-Kinema three-stage vacuum system. Reducing pressure allows a given amount of free fatty acids to be volatilized at a lower temperature and in a shorter period of time. The dryer therefore preferably operates at a temperature of from about 120° F. to about 150° F. and a pressure of from about 2 to about 50 mm Hg. More preferred is to operate the dryer at a temperature of from about 120° F. to about 140° F. and at a pressure of from about 5 to about 20 mm Hg. Most preferably, the dryer operates at a temperature of from about 120° F. to about 140° F. and a pressure of from about 2 to about 10 mm Hg.

The reaction mixture is distilled in the dryer for a time sufficient to convert the reaction mixture into approximately 40 to 50 percent by weight of a vapor phase and approximately 50 percent by weight of a liquid residue phase. The amount of time required will vary depending on the identity of the phosphatide-containing material from which the reaction mixture is derived. Generally, however, less than about 2 minutes at the operating conditions are required to produce the desired amounts of these two phases.

When distillation occurs in a deodorizer, it can be via a batch or a continuous process, but a continuous process is preferred because it provides more consistent temperature gradients. The deodorizer generally operates at a pressure of less than about 10 mm Hg and a temperature of from about 380° F. to about 500° F. Preferably, the deodorizer contains a plurality of trays arranged sequentially in any orientation, including vertical or horizontal. More preferably, the deodorizer is a stripping tower having trays spaced vertically from each other. As discussed above, reduced pressure can be generated via any convenient source. In distilling the reaction mixture in a deodorizer, the reaction is advantageously contacted with steam.

The vapor phase produced in distilling the reaction mixture is then condensed in a cooling apparatus to form a distillate containing at least about 97 percent by weight free fatty acids. Cooling can be accomplished either directly, as by mixing with a separate stream of distillate, or indirectly, as by a convenient means such as a heat exchanger.

Surprisingly, the distillate produced by the invention is white. Up to now, free fatty acids available as byproducts of vegetable oil refining have been limited to oil-derived free fatty acids. Oil-derived free fatty acids typically range in color from brown to light brown, having a Gardner color of from about 10 to about 6. The phosphatide-derived free fatty acids of the invention, however, have a snow-white appearance, which makes them unique among free fatty acids available as byproducts of vegetable oil refining.

Surprisingly also, the fatty acid chain length distribution in the phosphatide-derived free fatty acids of the invention does not match the fatty acid chain length distribution of the crude oil from which they are derived. Generally, the fatty acid chain length distribution in the phosphatide-derived free fatty acids of the invention is from about 10 to about 18 percent by weight palmitic acid (C16:0), from about 3 to about 6 percent by weight stearic acid (C18:0), from about 9 to about 19 percent by weight oleic acid (C18:1), from about 50 to about 60 percent by weight linoleic acid (C18:2), and from about 4 to about 10 percent by weight linolenic acid (C18:3). Typically, the phosphatide-derived free fatty acids of the invention contain about 17.5 percent by weight palmitic acid (C16:0), about 10.5 percent by weight oleic acid (C18:1), and about 58 percent by weight linoleic acid (C18:2). By contrast, typical oil-derived free fatty acids obtained by prior methods contain about 10 percent by weight palmitic acid (C16:0), about 22 percent by weight oleic acid (C18:1), and about 53 percent by weight linoleic acid (C18:2).

Another distinction of the phosphatide-derived free fatty acids of the invention is that they contain palmitic and oleic acids in a ratio of at least about 1.5:1. By contrast, oil-derived free fatty acids generally contain palmitic and oleic acids in a ratio of only about 0.5:1 or less.

All documents, e.g., patents, journal articles, and textbooks, cited above or below are hereby incorporated by reference in their entirety.

One skilled in the art will recognize that modifications may be made in the present invention without deviating from the spirit or scope of the invention. The invention is illustrated further by the following examples, which are not to be construed as limiting the invention in spirit or scope to the specific procedures or compositions described therein.

EXAMPLE 1

An organic acid-treated phosphatide phase obtained via citric acid refining of soybean oil and having a pH of about 3 was held at acid pH for about 6 hours. The resulting reaction mixture was then distilled in a deodorizer operating at a pressure of about 4 mm Hg and a temperature of about 440° F. The resulting vapor phase was condensed in a heat exchanger to form a distillate in an amount of about 40 percent by weight based on the weight of reaction mixture.

The distillate was snow-white and contained free fatty acids in the relative amounts shown below:
%C16:0 17.7
%C18:0 4.4
%C18:1 10.6
%C18:2 58.3
%C18:3 8.0

EXAMPLE 2

An organic acid-treated phosphatide phase obtained via citric acid refining of soybean oil and having a pH of about 3 was held at acid pH for about 6 hours. The resulting reaction mixture was then distilled in a dryer operating at a pressure of about 2 mm Hg and a temperature of about 460° F. The resulting vapor phase was condensed in a heat exchanger to form a distillate in an amount of about 40 percent by weight based on the weight of reaction mixture. The distillate was snow-white and contained free fatty acids in the relative amounts shown below:
%C16:0 17.9
%C18:0 4.3
%C18:1 9.6
%C18:2 57.6
%C18:3 8.3

The invention and the manner and process of making and using it, are now described in such full, clear, concise and exact terms as to enable any person skilled in the art to which it pertains, to make and use the same. Although the foregoing describes preferred embodiments of the present invention, modifications may be made therein without departing from the spirit or scope of the present invention as set forth in the claims. To particularly point out and distinctly claim the subject matter regarded as invention, the following claims conclude this specification.

What we claim is:

1. A process for recovering fatty acids from an organic-acid treated phosphatide, comprising:

(a) providing an phosphatide-containing material selected from the group consisting of a phosphatide-enriched aqueous phase obtained from an organic acid refining process, an organic acid-treated phosphatide phase obtained from an organic acid refining process, or a mixture thereof;

(b) maintaining the phosphatide-containing material at acidic pH for a time sufficient to produce a reaction mixture containing free fatty acids;

(c) distilling the reaction mixture for a time sufficient to convert the reaction mixture into a vapor phase and a liquid residue; and (d) condensing the vapor phase to form a distillate containing at least about 97 percent by weight free fatty acids.

2. The process of claim 1, wherein the reaction mixture is maintained at a pH of from about 3 to about 5.

3. The process of claim 1, wherein the phosphatide-containing material remains at acidic pH for a time of from about 3 to about 9 hours.

4. The process of claim 1, wherein step (c) distilling occurs in a dryer utilizing an operating pressure of less than about 4 mm Hg and a temperature of less than about 450° F.

5. The process of claim 1, wherein step (c) distilling occurs in a deodorizer utilizing an operating pressure of less than about 4 mm Hg and a temperature of less than about 440° F.

6. The process of claim 1, wherein the amount of distillate produced is greater than about 40 percent by weight of the reaction mixture.

7. The process of claim 1, wherein the distillate contains palmitic and oleic acids in a ratio of at least about 1.5:1.

8. The process of claim 1, wherein the distillate is white.

* * * * *